United States Patent [19]

Mar et al.

[11] Patent Number: 5,411,544
[45] Date of Patent: May 2, 1995

[54] DEFIBRILLATION LEAD WITH IMPROVED MECHANICAL AND ELECTRICAL CHARACTERISTICS

[75] Inventors: Craig E. Mar; M. Elizabeth Bush, both of Fremont; Benjamin D. Pless, Menlo Park, all of Calif.

[73] Assignee: Ventritex, Inc., Sunnyvale, Calif.

[21] Appl. No.: 145,839

[22] Filed: Nov. 2, 1993

[51] Int. Cl.$^6$ ............................................. A61N 1/05
[52] U.S. Cl. ........................................................ 607/122
[58] Field of Search ............ 128/642; 607/96, 98–100, 607/103, 113, 115–132, 154, 155, 156

[56] References Cited

U.S. PATENT DOCUMENTS

| | | | |
|---|---|---|---|
| Re. 32,204 | 7/1986 | Halvorsen | 128/642 |
| 3,942,536 | 3/1976 | Mirowski et al. | 128/419 |
| 4,030,509 | 6/1977 | Heilman et al. | 128/419 |
| 4,156,429 | 5/1979 | Amundson | 128/419 |
| 4,161,952 | 7/1979 | Kinney et al. | 128/786 |
| 4,291,707 | 9/1981 | Heilman et al. | 128/784 |
| 4,352,360 | 10/1982 | King | 607/121 |
| 4,606,354 | 8/1986 | Jacob | 607/116 |
| 4,784,159 | 11/1988 | Szilagyi | 607/116 |
| 4,844,099 | 7/1989 | Skalsky et al. | 128/785 |
| 4,848,352 | 7/1989 | Pohndorf et al. | 607/122 |
| 4,998,975 | 3/1991 | Cohen et al. | 128/419 |
| 5,007,436 | 4/1991 | Smits | 128/786 |
| 5,016,808 | 5/1991 | Heil, Jr. et al. | 228/176 |
| 5,042,143 | 8/1991 | Holleman et al. | 29/825 |
| 5,223,309 | 6/1993 | Farivar et al. | 427/525 |
| 5,226,260 | 7/1993 | Mar et al. | 51/319 |
| 5,293,869 | 3/1994 | Edwards et al. | 128/642 |

FOREIGN PATENT DOCUMENTS

| | | | |
|---|---|---|---|
| 0064289 | 11/1987 | European Pat. Off. | 607/116 |
| 2822829 | 11/1979 | Germany | 607/122 |
| 4112936 | 10/1991 | Germany | 607/122 |
| 50-32542 | 3/1980 | Japan | 607/115 |
| 1132957 | 1/1985 | U.S.S.R. | 607/115 |

OTHER PUBLICATIONS

"Advanced Materials & Processes", Surface engineering of Spire, vol. 138, No. 6, Dec. 1990.
"Surface Modification of Polymers and Ceramics" Hirvonen, Spire Corporation.
"Highly Adherent IR and IR Oxide Coatings on Neural Electronics", Phase 1 Final Report, NIH Contract No. 1 R43 NS26205-01, Keith O. Legg, Apr. 4, 1989.
Spire Corporation Annual Report (1991).

*Primary Examiner*—William E. Kamm
*Assistant Examiner*—Marianne Parker
*Attorney, Agent, or Firm*—Mark J. Meltzer; Steven M. Mitchell; M. Elizabeth Bush

[57] ABSTRACT

An implantable cardiac defibrillation lead is provided in which surface modification and deposition techniques are utilized to provide improved electrical and mechanical characteristics. The surface of an electrode can thereby be matched to the heart tissue for biocompatibility while at the same time providing for the appropriate electrical and mechanical characteristics of the electrode material.

2 Claims, 1 Drawing Sheet

DEFIBRILLATION LEAD WITH IMPROVED MECHANICAL AND ELECTRICAL CHARACTERISTICS

FIELD OF THE INVENTION

The present invention relates generally to leads used for cardiac defibrillation, and more particularly to leads that are implanted and used with an implantable defibrillator.

BACKGROUND OF THE INVENTION

It is well known that cardiac arrhythmias may be controlled with devices such as implantable defibrillators. Previous endocardial lead electrodes used with such devices are disclosed in Mirowski et al., U.S. Pat. No. 3,942,536 and Kinney et al., U.S. Pat. No. 4,161,952, and epicardial electrodes are disclosed in Heilman et al., U.S. Pat. No. 4,030,509 and Heilman et al., U.S. Pat. No. 4,291,707.

In U.S. Pat. No. 5,016,808 to Heil, Jr. et al., an implantable endocardial defibrillation lead is suggested wherein a conductive deposited electrode is produced by plating or vapor deposition of a conductive material onto a tubular body.

Endocardial lead electrodes have several functional requirements which must be met. Firstly, the electrodes must be able to deliver large amounts of electrical current. Secondly, it is desirable that the electrodes have large surface areas so that the energy can be delivered over a large area of the heart and the current can be evenly distributed. In so doing, current density is decreased and the chance of damaging heart tissues is significantly lessened. Thirdly, the electrodes must be flexible and fatigue resistant to provide ease of implantation and avoid lead fracture.

Because of their location within the heart, electrodes must endure constant motion and millions of flex cycles.

Past implantable electrodes have been made with materials such as titanium that are biocompatible. However, these biocompatible materials may be deficient in other areas such as anodic corrosion resistance, current carrying capability or mechanical fatigue properties.

Accordingly, there is a need for an improved implantable defibrillation electrode that is able to deliver large amounts of current over large surface areas. In addition there is a need for a defibrillation electrode that allows the current to be evenly distributed. There is also a need for a defibrillation electrode that has improved fatigue resistance over previously known electrodes. The present invention satisfies the above-identified needs.

SUMMARY OF THE INVENTION

The present invention comprises an implantable endocardial defibrillation lead having an electrode comprising an insulating biocompatible catheter that is modified by surface modification techniques and an electrically conductive material applied to the catheter material utilizing a surface deposition technique. With the advent of surface deposition and surface modification technologies, the various characteristics of many materials can be changed to meet specific requirements.

What is meant by surface modification in the context of this application is a system for changing the mechanical and/or electrical characteristic of the materials used for the electrode or lead body to meet specific requirements. What is meant by surface deposition is depositing and/or bonding to a biocompatible surface an electrically conductive material. The deposition process can be, for example, sputtering, ion beam deposition, ion beam assisted deposition (IBAD), chemical vapor deposition (CVD), plasma vapor deposition (PVD) or other processes that can be used with the biocompatible material. Surface modification may be by ion bombardment, ion beam deposition, etching or other known techniques.

Using surface modification techniques, the surface of the biocompatible material may be etched or the like to increase its surface roughness. This in turn will promote faster cell growth, causing the electrode to adhere in a specific and desirable location of the heart, thus diminishing the possibility of unwanted electrode movement. The modified surface may also cause less tissue irritation thus reducing scar tissue generation and reducing defibrillation thresholds. Additionally, greater electrode surface area may be provided.

By utilizing surface modification and surface deposition techniques, electrode materials may be chosen that are optimal in biocompatibility, mechanical properties (such as fatigue life), conductivity and corrosion properties (such as anodic corrosion resistance). This may be accomplished by using several deposition layers having, for example, a lower fatigue resistant layer and an upper anodic corrosion resistance layer. In particular the electrode may have a base electrode material with good mechanical properties (such as MP35N). By using the surface deposition techniques, the base electrode material and insulating catheter can be modified or coated with another material which has good biocompatibility and corrosion resistance and conductivity (such as platinum). The coating will be electrically attached to the base electrode material as a result of the deposition process.

In another embodiment, the electrode material such as platinum is deposited directly on the insulating biocompatible material utilizing surface deposition techniques.

DETAILED DESCRIPTION

The present invention relates to an improvement in an implantable endocardial lead defibrillation electrode. The following description is presented to enable one of ordinary skill in the art to make and use the invention as provided in the context of a particular application and its requirements. Various modifications to the preferred embodiments will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

Figure 1:
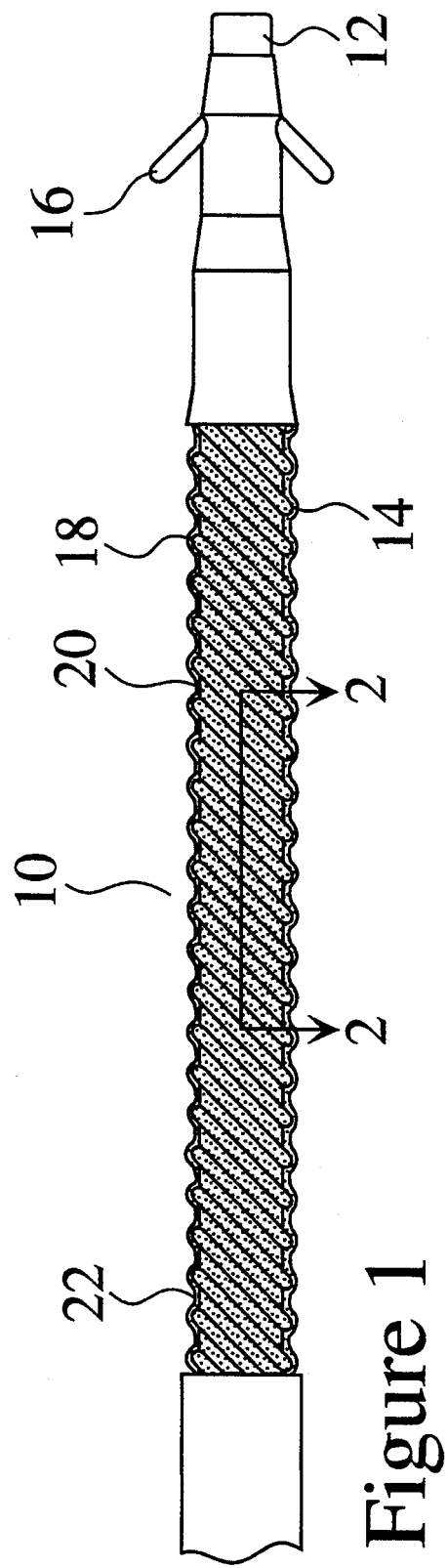
FIG. 1 shows a side view of an embodiment of an endocardial defibrillator electrode in accordance with the present invention.

FIG. 1 shows an endocardial lead assembly 10 in accordance with the present invention. The assembly 10 includes a defibrillation electrode 14 and a pacing electrode 12. Flexible tines 16 serve to secure the assembly to the trabeculae of the patient's heart following transvenous implantation. A metal coil 18 is wrapped around a catheter 20 to form defibrillation electrode 14. The catheter 20 is made of an elastomeric tubing such as silicone. Other, non elastic materials may also be used. Metal coil 18 is preferably MP35N or platinum/iridium alloy wire which is coupled at the proximal end to a conductor, preferably a coil running through the lumen of catheter 20. At the proximal end of lead assembly 10, the conductor is electrically coupled to a connector adapted for connection to an implantable defibrillator. A conductive coating 22 is applied to metal coil 18 and catheter 20. Platinum is the preferred material for coating 22. In this embodiment, the metal coating 22 can be deposited on catheter 20 using ion beam assisted deposition (IBAD) while rotating the lead assembly 10 to provide even coverage of the metal layer. The IBAD technique improves the adhesion properties of the coating by creating a transition layer of platinum atoms embedded in the surface of catheter 20. This may typically be accomplished by evaporative deposition of platinum at the same time as the surface is bombarded with gaseous ions such as argon. In an alternative embodiment, the material of the catheter 20 to which the electrode is applied in the form of coil 18 and metal coating 22 may be conductive rubber or other flexible conductive material.

Through the use of surface deposition and surface modification techniques the mechanical properties, electrical properties and surface characteristics of lead assembly 10 can be optimized. Accordingly, catheter 20 can be optimized for biocompatibility utilizing surface modification techniques of ion bombardment or ion implantation such as are described in U.S. Pat. No. 5,223,309 to Farivar et al., which patent is incorporated herein by reference. Alternatively, etching may be used to increase the surface roughness and improve biocompatibility. This will promote faster cell growth and will help adhere the electrode in a specific and desirable location in the heart. Other portions of the lead body may be modified with the surface modification technique to promote fibrosis. For example, it may be possible to avoid the use of a suture sleeve at the location where the lead is introduced into the venous system by modifying this surface to promote fibrosis.

Coating 22 can be applied utilizing a variety of techniques such as ion beam deposition, ion beam assisted deposition (IBAD), chemical vapor deposition, sputtering or other types of operating processes that can be integrated with biocompatible material. The adhesion properties of the coating 22 may be improved by using an inter layer such as titanium to promote bonding. The surface modification may be accomplished either before or after deposition of conductive coating 22. If performed before coating, the coating will follow the contour of the modified surface 5 after, the surface of coating 22 will be textured to promote tissue adhesion and electrode fixation.

Figure 2:
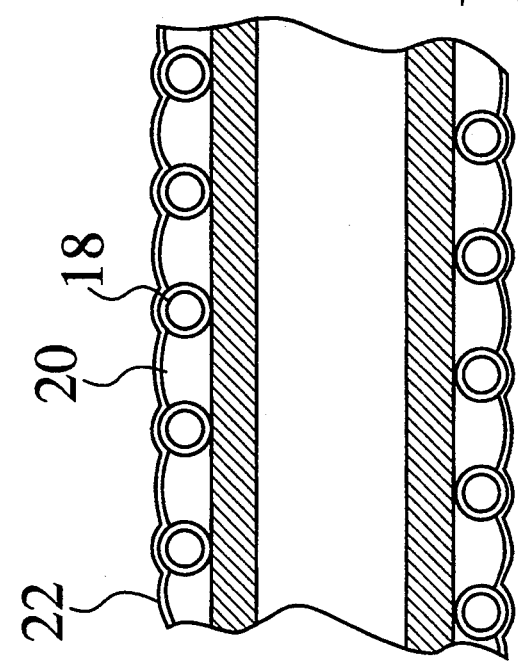
FIG. 2 is a sectional view of the electrode of FIG. 1.

Referring now to FIG. 2, what is shown is an enlarged cross sectional view 2—2 of electrode 10. The coil 18 is embedded in an insulating material on catheter 20 in a manner such as is described in U.S. Pat. No. 5,226,260 to Mar et al., which patent is incorporated herein by reference. As is seen, a metal surface coating 22 is placed thereon to facilitate current conductivity as well as to provide improved mechanical properties.

The structure to be coated could be many other bulk electrode materials on insulating materials, for example spaced metal rings on a catheter, as described in U.S. Pat. No. 3,942,536 to Mirowski et al., or wound spring wire on a catheter, as described in U.S. Pat. No. 4,161,952 to Kinney et al. Another preferred embodiment includes a coiled coil electrode wherein one or more coiled wires are spirally wound around the catheter. Such an electrode configuration is described in copending U.S. patent application Ser. No. 08/126,619, filed Sep. 24, 1993, which copending application is assigned to the assignee of the present application and which is incorporated herein by reference. The use of the various wire, coil or spring base electrode materials for the defibrillation electrode improve the ease with which the conductive coating 22 is electrically connected to the lead conductor. Additionally, the system redundancy is improved.

While the particular description above contains many specifics, the scope of the invention should not be limited to these details. Accordingly, although the present invention has been described in accordance with the embodiments shown, one of ordinary skill in the art will recognize that there could be variations to the embodiment and those variations would be within the spirit and scope of the present invention. Accordingly, many modifications may be made by one of ordinary skill without departing from the spirit and scope of the present invention, the scope of which is defined solely by the following claims.

What is claimed:

1. A defibrillation lead comprising:
   a flexible polymeric catheter having an outer roughened surface;
   a partially exposed metal coil embedded in a portion of said flexible polymeric catheter;
   a first layer of electrically conductive material deposited by a surface deposition technique on said exposed portion of said metal coil and to the portion of said catheter containing said partially embedded metal coil wherein an electrical connection of said metal coil and said first layer of electrically conductive material is formed; and
   terminal means for connection to a defibrillator, electrically joined to said first layer of electrically conductive material and to said partially embedded metal coil.

2. The defibrillation lead of claim 1 wherein the portion of the catheter into which said metal coil is partially embedded and on which said first layer of electrically conductive material is deposited comprises a flexible conductive material.

* * * * *